United States Patent
Kazemizadeh et al.

(10) Patent No.: US 9,586,918 B2
(45) Date of Patent: Mar. 7, 2017

(54) UNSATURATED FATTY ACID ESTER-BASED COMPOSITIONS USEFUL AS PLASTIC ADDITIVES

(71) Applicant: Arkema Inc., King of Prussia, PA (US)

(72) Inventors: Mohammad R. Kazemizadeh, Blooming Prairie, MN (US); David E. Maixner, Blooming Prairie, MN (US)

(73) Assignee: Arkema Inc., King of Prussia, PA (US)

( * ) Notice: Subject to any disclaimer, the term of this patent is extended or adjusted under 35 U.S.C. 154(b) by 0 days.

(21) Appl. No.: 14/769,489

(22) PCT Filed: Feb. 17, 2014

(86) PCT No.: PCT/US2014/016688
§ 371 (c)(1),
(2) Date: Aug. 21, 2015

(87) PCT Pub. No.: WO2014/130391
PCT Pub. Date: Aug. 28, 2014

(65) Prior Publication Data
US 2016/0009673 A1  Jan. 14, 2016

Related U.S. Application Data

(60) Provisional application No. 61/768,653, filed on Feb. 25, 2013.

(51) Int. Cl.
| | | |
|---|---|---|
| *C07D 303/42* | (2006.01) | |
| *C07D 303/16* | (2006.01) | |
| *C07D 301/19* | (2006.01) | |
| *C08K 5/1515* | (2006.01) | |
| *C08G 59/02* | (2006.01) | |
| *C08G 59/14* | (2006.01) | |
| *C08G 59/16* | (2006.01) | |
| *C08G 59/32* | (2006.01) | |

(52) U.S. Cl.
CPC ......... *C07D 303/42* (2013.01); *C07D 301/19* (2013.01); *C07D 303/16* (2013.01); *C08G 59/027* (2013.01); *C08G 59/1444* (2013.01); *C08G 59/1455* (2013.01); *C08G 59/32* (2013.01); *C08K 5/1515* (2013.01)

(58) Field of Classification Search
CPC .................................................. C07D 303/42
See application file for complete search history.

(56) References Cited

U.S. PATENT DOCUMENTS

| | | | |
|---|---|---|---|
| 2,857,349 A | 10/1958 | Greenspan et al. | |
| 3,008,911 A | 11/1961 | Douglas | |
| 3,051,672 A | 8/1962 | Rowland et al. | |
| 3,190,899 A | 6/1965 | Walton et al. | |
| 3,256,225 A | 6/1966 | Nevin | |
| 3,262,953 A | 7/1966 | Findley et al. | |
| 3,479,308 A | 11/1969 | Gattenby et al. | |
| 5,324,846 A * | 6/1994 | Hirshman | C08K 5/1515 554/121 |
| 6,274,748 B1 * | 8/2001 | Young | C07C 303/22 554/69 |
| 6,734,241 B1 | 5/2004 | Nielsen et al. | |
| 6,797,753 B2 | 9/2004 | Benecke et al. | |
| 6,949,597 B2 | 9/2005 | Nielsen et al. | |
| 7,544,763 B2 * | 6/2009 | Kazemizadeh | C08G 18/36 528/1 |
| 9,034,965 B2 * | 5/2015 | Kazemizadeh | C08K 5/0016 524/114 |
| 2010/0010126 A1 | 1/2010 | Ruschel et al. | |
| 2012/0214920 A1 | 8/2012 | Frenkel | |

FOREIGN PATENT DOCUMENTS

| | | |
|---|---|---|
| GB | 741492 | 12/1955 |
| WO | WO 2012/019073 A1 | 2/2012 |

OTHER PUBLICATIONS

Nutrition Data, "Oil, soybean, salad or cooking" Publication (online) Jul. 30, 2010 (retrieved on Apr. 21, 2014), Retrieved from the internet <URL: http://web.archive.org/web/20100730053255/http://nutritiondata.self.com/facts/fats-and-oils/507/2>. p. 2, Fats & Fatty acids.

* cited by examiner

*Primary Examiner* — Golam M M Shameem
(74) *Attorney, Agent, or Firm* — Lynn B. Morreale

(57) ABSTRACT

Compositions useful as plastic additives may be prepared from renewable resources such as vegetable oils by functionalizing an unsaturated fatty acid ester with epoxy, acyloxy, and optionally alkoxy groups.

11 Claims, 2 Drawing Sheets

UNSATURATED FATTY ACID ESTER-BASED COMPOSITIONS USEFUL AS PLASTIC ADDITIVES

CROSS-REFERENCE TO RELATED APPLICATIONS

This application is a national stage application under 35 U.S.C. §371 of PCT/US2014/016688, filed Feb. 17, 2014, which claims benefit to U.S. patent application Ser. No. 61/768,653, filed on Feb. 25, 2013.

FIELD OF THE INVENTION

The invention relates to compositions derived from unsaturated fatty acid esters such as triglycerides which are useful as additives (e.g., as plasticizers and/or acid scavengers) for thermoplastic polymers as well as in other end-use applications.

BACKGROUND OF THE INVENTION

Thermoplastic polymers, such as polyvinyl chloride (PVC) for example, are often utilized in one or both of two general forms: substantially unplasticized and plasticized. The substantially unplasticized forms of thermoplastic polymers may be utilized in applications in which high resistance to chemical substances is required. The plasticized forms of thermoplastic polymers are commonly used in applications where flexibility and pliability are among the most important physical characteristics. These physical characteristics are achieved by compounding a thermoplastic polymer such as PVC with one or more materials which serve as plasticizers following their addition to the thermoplastic resin. Broadly defined, plasticizers are high boiling point liquids. These liquids do not evaporate from the matrices they are added to, but rather remain in the polymer matrix to preserve flexibility, pliability, and adhesiveness. Plasticizers currently in industrial use generally are petroleum-derived phthalates and benzoate compounds. Dioctyl phthalate (DOP) and diallyl phthalate (DAP) are examples of petroleum-derived compounds commonly used as plasticizers for PVC.

Petroleum-derived plasticizers may be subject to several significant limitations. In addition to being processed from a nonrenewable source, such plasticizers may be expensive to produce due to fluctuations in the price and availability of crude oil. Furthermore, petroleum-derived plasticizers such as DOP are suspected to disrupt human endocrine activity. Therefore, it may be desirable to limit the use of petroleum-derived plasticizers in certain situations, especially when the plasticized product comes into human contact at ambient temperature and especially at elevated temperature. Thus, there is a need for a low-cost, non-toxic, environmentally safe alternative to the petroleum-derived plasticizers that are currently incorporated into consumer products. Plasticizers which are derived from vegetable oils provide such an alternative.

However, unmodified vegetable oils are largely incompatible with thermoplastic polymers such as polyvinyl chloride resin. Certain types of modified derivatives of vegetable oils, such as epoxidized soybean oil, have been investigated as possible plasticizers, as exemplified in the disclosures of U.S. Pat. Nos. 6,734,241; 6,797,753; and 6,949,597 and U.S. Pat. Publication No. 2010/0010126. Although such derivatives may provide certain advantages over unmodified vegetable oils, there is continued need for even further improvement in the performance and characteristics of plasticizers obtained from renewable resources such as plants.

SUMMARY OF THE INVENTION

The present invention provides compounds and compositions useful as additives for plastics which may be characterized as fatty acid esters functionalized with epoxy, acyloxy, and optionally alkoxy groups and which may be prepared by derivatization of unsaturated fatty acid esters.

One aspect of the invention provides a compound comprised of a fatty acid ester moiety, wherein the fatty acid ester moiety comprises at least one epoxy group and wherein the fatty acid ester moiety is substituted with at least one acyloxy group and at least one alkoxy group which are substituted on adjacent carbon atoms in the fatty acid ester moiety. The fatty acid ester moiety may, for example, be selected from the group consisting of fatty acid monoesters, monoglycerides, diglycerides, triglycerides, and fatty acid esters of polyols other than glycerin.

The at least one acyloxy group may be a C2-C25 aliphatic acyloxy group, in one embodiment of the invention. The at least one acyloxy group may have a structure R—C(=O)—O—, wherein R is a straight chain, branched or alicyclic, saturated or unsaturated hydrocarbyl group containing one to 23 carbon atoms. In one particular aspect, the at least one acyloxy group may be an acetoxy group. The at least one alkoxy group may, for example, be a C1-C24 alkoxy group or have a structure R1-O—, wherein R1 is a straight chain, branched or alicyclic, saturated or unsaturated hydrocarbyl group containing one to 23 carbon atoms (in particular, one to ten carbon atoms). The compound in one embodiment may comprise a first fatty acid ester moiety and second fatty acid ester moiety which are linked together through a polyfunctional alkoxy group a polyfunctional acyloxy group, or a polyfunctional alkoxy/acyloxy group.

Another aspect of the invention furnishes a method of making a composition useful as a plasticizer, comprising the steps of:

a) partially epoxidizing an unsaturated fatty acid ester to provide a partially epoxidized fatty acid ester product containing epoxy functionality and residual unsaturation;

b) reacting the partially epoxidized fatty acid ester product from step a) with at least one reactant selected from the group consisting of alcohols and carboxylic acids to provide a ring-opened fatty acid ester product containing hydroxyl functionality and residual unsaturation;

c) converting at least a portion of the hydroxyl functionality in the ring-opened fatty acid ester product from step b) to acyloxy functionality to provide an acylated fatty acid ester product containing residual unsaturation; and d) epoxidizing the acylated fatty acid ester product from step c).

The unsaturated fatty acid ester used in such a method may be selected from the group consisting of unsaturated fatty acid monoesters, unsaturated monoglycerides, unsaturated diglycerides, unsaturated triglycerides, and unsaturated fatty acid esters of polyols other than glycerin. For example, the unsaturated fatty acid ester may be an unsaturated vegetable oil, such as an unsaturated vegetable oil selected from the group consisting of canola oil, linseed oil, rapeseed oil, safflower oil, soybean oil, corn oil, sunflower oil, and sunflower oil and blends thereof. In various aspects of the invention, the unsaturated vegetable oil may contain at least 70%, at least 75% or at least 80% unsaturated fatty acid groups.

The present invention also relates to compositions produced by the aforementioned process.

In another aspect of the invention, a plasticized resin composition is provided which comprises at least one thermoplastic polymer and at least one compound in accordance with the foregoing description or a composition produced in accordance with the above-described process. A plasticized resin composition may be made by a method comprising combining at least one thermoplastic polymer and at least one such compound or composition.

Still other aspects of the invention relate to a composition useful as a plasticizer, comprising a fatty acid product derived from a fatty acid ester containing unsaturated fatty acid groups, wherein the unsaturated fatty acid groups have been at least partially reacted to provide epoxy, acyloxy and optionally alkoxy functionality in the fatty acid product or comprising a fatty acid ester product containing epoxy, acyloxy and optionally alkoxy functionality. The epoxy functionality may be present as a moiety within a fatty acid chain. The alkoxy functionality (if present) and the acyloxy functionality may be present as groups pendant to a fatty acid chain. An alkoxy group and an acyloxy group may be substituted on adjacent carbon atoms in a fatty acid chain. A first acyloxy group and a second acyloxy group, which may be the same as or different from each other, may be substituted on adjacent carbon atoms in a fatty acid chain. The fatty acid ester product may be derived from a fatty acid ester starting material selected from the group consisting of unsaturated fatty acid monoesters, unsaturated monoglycerides, unsaturated diglycerides, unsaturated triglycerides, and unsaturated fatty acid esters of polyols other than glycerin. The acyloxy functionality may comprise one or more $C_2$-$C_{25}$ aliphatic acyloxy groups, e.g., the acyloxy functionality may comprise one or more acyloxy groups having a structure R—C(=O)—O—, wherein R is a straight chain, branched or alicyclic, saturated or unsaturated hydrocarbyl group containing one to 23 carbon atoms. As an example, the acyloxy functionality may comprise acetoxy groups. If present, the alkoxy functionality, in one embodiment, may comprise one or more $C_1$-$C_{24}$ alkoxy groups. For example, the alkoxy functionality may comprise one or more alkoxy groups having a structure R1-O—, wherein R1 is a straight chain, branched or alicyclic, saturated or unsaturated hydrocarbyl group containing one to 23 carbon atoms. R1 in one aspect of the invention is a straight chain saturated hydrocarbyl group containing one to ten carbon atoms. The alkoxy functionality may comprise at least one polyfunctional alkoxy group (i.e., a group containing two or more alkoxy functional groups), wherein the polyfunctional alkoxy group may serve to link together two or more fatty acid groups. Likewise, the acyloxy functionality may comprise at least one polyfunctional acyloxy group (i.e., a group containing two or more acyloxy functional groups), which may also serve to link together two or more fatty acid groups.

The above-described composition may be used to produce a plasticized resin composition, comprising at least one thermoplastic polymer and at least one such composition. The invention thus provides a method of making a plasticized resin composition, comprising combining at least one thermoplastic polymer and at least one such composition.

The above-mentioned compounds and compositions have utility as full or partial replacements for phthalates and other types of conventional plasticizers in polymer formulations, particularly polyvinyl chloride (PVC) formulations. In addition to functioning as plasticizers, they may also act as acid scavengers in such formulations, thereby helping to stabilize the formulations against degradation due to residual or generated acid such as HCl. The compounds and compositions provided by the present invention may also be employed as lubricants or functional fluids or components of lubricants or functional fluids, particularly in applications such as metal working that generally require the use of compositions providing both lubricating and acid scavenging properties. Additionally, the unsaturated fatty acid ester derivatives of the present invention are useful as components of personal care products such as, for example, shampoos, conditioners, lotions, creams, cosmetics, insect repellants, sunscreens and the like as well as other products where phthalate esters are conventionally utilized.

The Figures are provided herein for illustrative, exemplary purposes only and are not intended to limit the scope of the invention in any way.

DETAILED DESCRIPTION OF THE INVENTION

Exemplary General Method of Preparation

Figure 1:
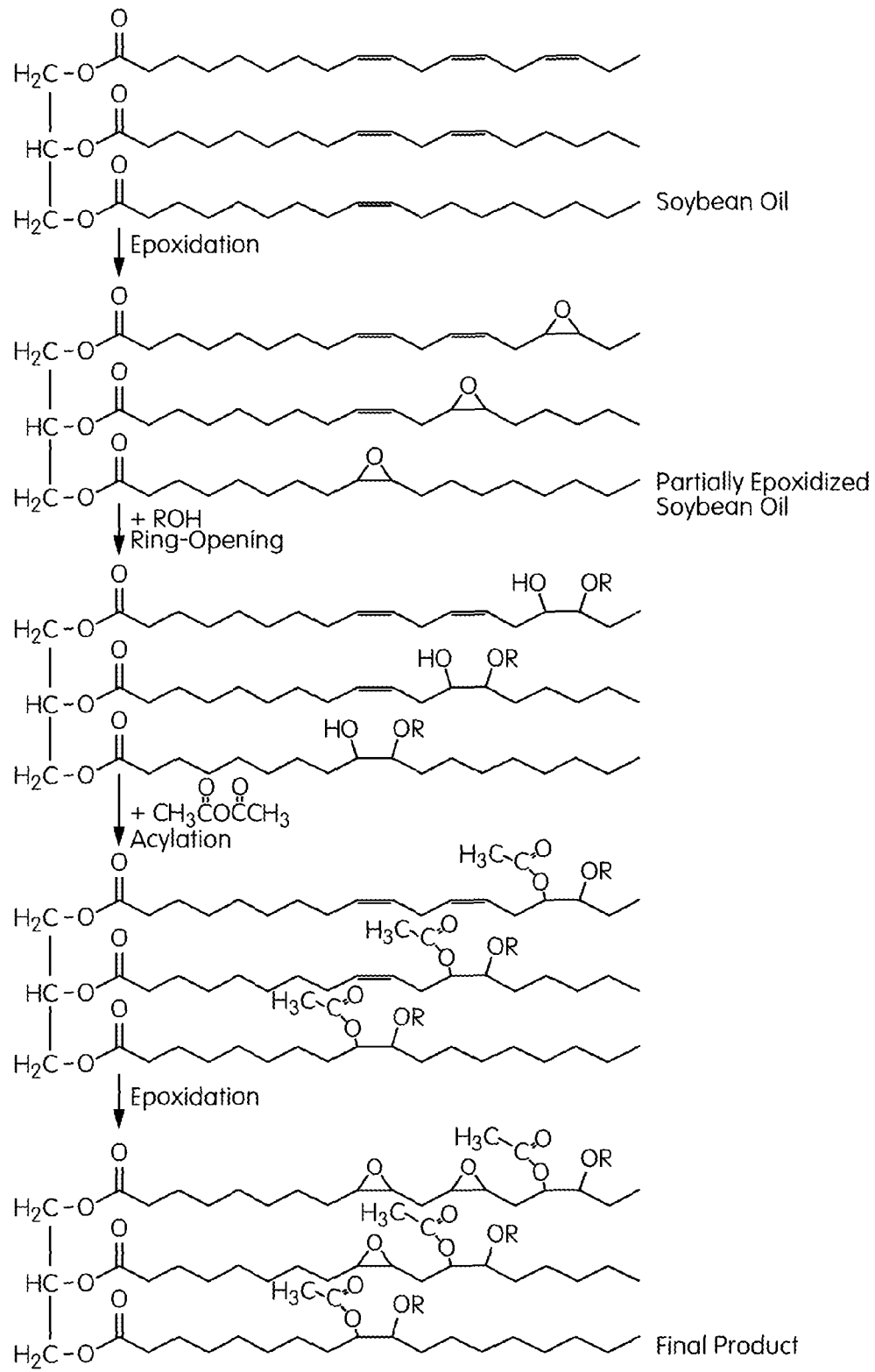
FIG. 1 outlines in illustrative schematic form how an individual unsaturated triglyceride may be converted into a compound containing epoxy, acyloxy and alkoxy functionality in accordance with the invention.
Figure 2:
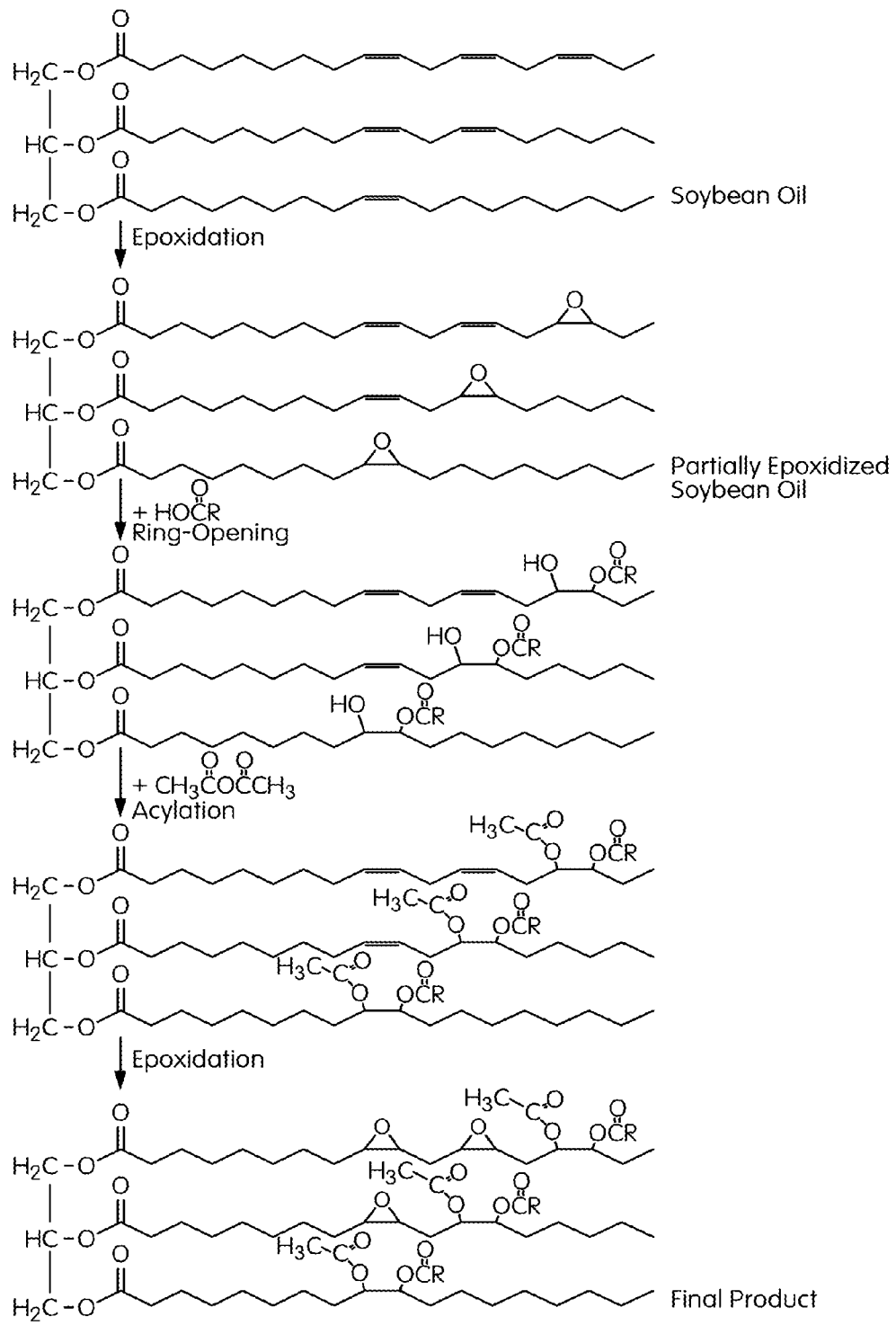
FIG. 2 outlines in illustrative schematic form how an individual unsaturated triglyceride may be converted into a compound containing epoxy and acyloxy functionality in accordance with the invention, wherein two acyloxy functional groups (which may be the same as or different from each other) are substituted on adjacent carbon atoms in the compound.

The compounds and compositions of the present invention may be prepared from unsaturated fatty acid esters using generally the sequential steps of partial epoxidation (wherein a portion of the carbon-carbon double bonds present in the unsaturated fatty acid ester are converted to epoxy groups), ring-opening of at least a portion of the epoxy groups with an alcohol and/or carboxylic acid, acylation of at least a portion of the hydroxyl groups generated in the ring-opening step, and a further epoxidation step wherein at least a portion of the remaining sites of unsaturation are converted into epoxy groups. The process flow chart set forth in FIG. 1 illustrates how soybean oil, a representative unsaturated fatty acid ester, may be reacted in accordance with the methods of the present invention to yield a product containing epoxy, acyloxy and alkoxy functional groups on the fatty acid moieties of the triglyceride. The acyloxy groups which are thereby introduced are in addition to the ester functional groups present in the starting unsaturated fatty acid ester. A similar exemplary process is set forth in FIG. 2, except that the product obtained contains epoxy and acyloxy functional groups, but no alkoxy groups, on the fatty acid moieties of the triglyceride. In this process, ring-opening of epoxide rings is carried out with a carboxylic acid, rather than an alcohol as illustrated in FIG. 1.

Starting Materials

The unsaturated fatty acid ester starting material may be any compound comprising at least one unsaturated fatty acid group and at least one ester group. Other types of groups may also be present in the unsaturated fatty acid ester. For example, the unsaturated fatty acid ester may contain at least one unsaturated fatty acid group and at least one saturated fatty acid group. The unsaturated fatty acid ester may contain two, three, four, five or more unsaturated fatty acid groups, which may be the same as or different from each other. Suitable unsaturated fatty acid groups may generally contain from six to 24 carbon atoms and may contain one, two or more sites of unsaturation (carbon-carbon double bonds) per group. The fatty acid group thus may be a monounsaturated or polyunsaturated fatty acid group. The carbon-carbon double bonds may have cis or trans configurations. The unsaturated fatty acid groups may be prepared synthetically or may be derived from natural sources such as triglycerides found in vegetable oils and fats and animal oils and fats. Illustrative unsaturated fatty acid groups useful in the present invention include, but are not limited to, oleyl (corresponding to oleic acid), linoleyl (linolenic acid), palmitoleyl (palmitoleic acid), myristoleyl (myristoleic acid), arachinonyl (arachinoic acid), linolenyl (linolenic acid), sapienyl (sapienic acid), vaccenyl (vaccenic acid), eicosapentaenyl (eicosapentaenic acid), erucyl (erucic acid) and docosahexaenyl (docosahexaenic acid). It is also possible for the unsaturated fatty acid group to contain or be substituted with other functional groups such as hydroxyl groups. Where the unsaturated fatty acid ester contains a plurality of fatty acid groups, mixtures of different unsaturated fatty acid groups may be present within the same molecule. The present invention may also employ mixtures of different unsaturated fatty esters as a starting material. Moreover, the starting material may contain, in addition to one or more unsaturated fatty acid esters, other types of compounds, in particular saturated fatty acid esters.

Where one or more saturated fatty acid groups are present in the unsaturated fatty acid ester, such groups may, for example, contain six to 24 carbon atoms per group. In various embodiments of the invention, the composition of the fatty acid ester starting material is selected such that at least 50%, at least 60%, at least 70%, at least 80%, at least 90% or even 100% of the fatty acid groups present are unsaturated fatty acid groups.

The fatty acid ester may be a mono-ester (containing just one ester linkage per molecule), a di-ester, a tri-ester, a tetra-ester or an ester containing five or more ester groups per molecule.

Alkyl esters of unsaturated fatty acids, such as those obtained by condensing an aliphatic alcohol with an unsaturated fatty acid or transesterification of an unsaturated triglyceride with an aliphatic alcohol, constitute a type of mono-ester useful as an unsaturated fatty acid ester in the present invention. The aliphatic alcohol may be, for example, a C1-C4 monoalcohol such as methanol or ethanol. Longer chain aliphatic alcohols may also be used, as may mixtures of different aliphatic alcohols. In one embodiment of the invention, methyl esters of unsaturated fatty acids derived from natural sources such as unsaturated vegetable oils are utilized. Unsaturated biodiesel may be used as a starting material, for example.

In another embodiment, unsaturated triglycerides derived from natural sources such as animals and plants may be employed. Such unsaturated triglycerides may be used as isolated or extracted from the natural source without chemical modification or fractionation or may be further treated or processed so as to alter their characteristics, provided they retain at least some degree of unsaturation. Illustrative examples of natural oils and fats which may suitably function as the fatty acid ester starting material of the present invention include, but are not limited to, canola oil, linseed oil, rapeseed oil, safflower oil, soybean oil, corn oil, sunflower oil, castor oil and sunflower oil as well as admixtures thereof and admixtures of such triglycerides with other types of unsaturated fatty acid esters (such as unsaturated mono- and di-glycerides, for example).

Unsaturated mono- and diglycerides and mixtures thereof may also be employed. Such substances comprise a glycerin moiety to which is attached, through ester linkages, one or two fatty acid groups, at least one of which is unsaturated.

In yet another embodiment of the invention, the unsaturated fatty acid ester starting material may be an unsaturated fatty acid ester of a polyol other than glycerin or a mixture of such substances. The polyol may be any compound containing two, three, four, five or more hydroxyl groups per molecule, at least one of which has been esterified with an unsaturated fatty acid. In one embodiment, the polyol is fully esterified (i.e., no hydroxyl groups are present). As previously discussed in connection with the unsaturated triglyceride, the unsaturated fatty acid ester of a polyol other than glycerin may contain one or more other types of ester groups, such as saturated fatty acid ester groups, in addition to the unsaturated fatty acid group(s). Suitable polyols include, but are not limited to, aliphatic polyols including diols such as 1,6-hexanediol, propylene glycol and ethylene glycol, triols such as trimethylolpropane, tetraols such as pentaerythritol, as well as sugars, sugar alcohols and the like.

Initial Partial Epoxidation Step

A portion of the sites of unsaturation present in the unsaturated fatty acid ester are converted to epoxy groups. Where the carbon-carbon double bond being epoxidized is present in the backbone of an unsaturated fatty acid group, the resulting epoxy group will likewise be part of the fatty acid group backbone. The site of unsaturation may, however, be pendent to the fatty acid group background, in which case the epoxy group obtained will also appear as a group pendant to the backbone.

In various embodiments of the invention, at least 10%, at least 20%, at least 30%, at least 40%, or at least 50% or more of the carbon-carbon double bonds present in the unsaturated fatty acid ester composition used as a starting material are epoxidized (converted to epoxy groups), provided that complete (100%) epoxidation is avoided. In other various embodiments of the invention, not more than 90%, not more than 80%, not more than 70%, not more than 60% or not more than 50% of the carbon-carbon double bonds are epoxidized.

The extent of epoxidation may, for example, be monitored by measuring the iodine value of the epoxidation reaction product and comparing such value to the iodine value of the starting material. The oxirane content of the reaction product may also be measured directly by standard analytical techniques.

Any suitable or known method for epoxidizing carbon-carbon double bonds may be employed, such as, for example, contacting the unsaturated fatty acid ester with hydrogen peroxide in the presence of an acid such as formic acid (optionally, with an organic solvent also being present) or with a peroxy acid for a time and at a temperature effective to achieve the desired extent of conversion of the sites of unsaturation to epoxy groups.

Ring-Opening Step

In the ring-opening step, the partially epoxidized fatty acid ester obtained from the initial epoxidation step is reacted with one or more alcohols and/or one or more carboxylic acids so as to open up at least a portion of the epoxy groups. As a result of such reaction, an epoxy group is ring-opened such that an ether group derived from the alcohol or an ester (acyloxy) group derived from the carboxylic acid is substituted on one carbon atom of the site of unsaturation and a hydroxy group derived from the oxygen atom of the epoxy group is substituted on the other carbon atom of the same site of unsaturation. The product of such reaction may be characterized as a ring-opened fatty acid ester product containing hydroxyl functionality and residual unsaturation. Acyloxy and/or alkoxy functionality is also present as a result of the reaction of the carboxylic acid and/or alcohol with the epoxy groups(s).

The properties and characteristics of the final product may be varied and controlled as may be desired by selecting the type of alcohol and/or carboxylic acid which is reacted with the partially epoxidized fatty acid ester. For example, the alcohol may be a short chain, medium chain or long chain alcohol. The alcohol may be straight chain or branched and may contain one or more alicyclic groups. In one embodiment, the alcohol is saturated, but in another embodiment the alcohol is unsaturated (with the sites of unsaturation thereby introduced possibly being at least partially epoxidized in the subsequently epoxidation step). The alcohol may contain heteroatoms other than the oxygen atom(s) of the hydroxyl group(s). For example, the alcohol may contain one or more ether linkages. The alcohol may be a C1-C24 mono-alcohol, including (without limitation) methanol, ethanol, n-propanol, isopropanol, n-butanol, sec-butanol, isobutanaol, t-butyl alcohol, n-hexanol, n-octanol, 2-ethyl hexanol, and the like and combinations thereof.

In one embodiment, a polyalcohol containing two or more hydroxyl groups per molecule is utilized, as either the sole alcohol or in admixture with one or more other polyols and/or one or more mono-alcohols (alcohols containing just one hydroxyl group per molecule). When such a polyalcohol is employed, the hydroxyl groups are capable of reacting with epoxy groups on two or more of the partially epoxidized unsaturated fatty acid ester obtained in the initial epoxidation step. The polyalcohol thus may function to link together two or more partially epoxidized unsaturated fatty acid molecules.

The carboxylic acid may be of any suitable structure. In one aspect of the invention, the carboxylic acid may be a monocarboxylic acid containing a branched, linear or cyclic aliphatic (saturated or unsaturated) hydrocarbyl group, such as a C1 to C23 alkyl group. Suitable carboxylic acids include, but are not limited to, short chain monocarboxylic acids such as acetic acid, propionic acid, butyric acid and the like as well as medium and longer chain monocarboxylic acids such as neooctanoic acid and fatty acids, in particular C8 to C24 saturated and unsaturated carboxylic acids. Combinations of different carboxylic acids may be utilized.

In one embodiment, a polycarboxylic acid containing two or more carboxylic acid groups per molecule is utilized, as either the sole carboxylic acid or in admixture with one or more monocarboxylic acids. When such a polycarboxylic acid is employed, the carboxylic acid groups are capable of reacting with epoxy groups on two or more molecules of the partially epoxidized unsaturated fatty acid ester obtained in the initial epoxidation step. The polycarboxylic acid thus may function to link together two or more partially epoxidized unsaturated fatty acid molecules.

In another embodiment, a reactant containing both one or more carboxylic acid groups and one or more hydroxyl groups per molecule is utilized, either as the sole reactant used in the ring-opening step or in admixture with one or more reactants containing only hydroxyl groups and/or only carboxylic acid groups. Such an acid- and hydroxy-functionalized reactant is capable of reacting with epoxy groups on two or more molecules of the partially epoxidized unsaturated fatty acid ester, thus functioning to link together two or more partially epoxidized unsaturated fatty acid molecules.

Mixtures of different alcohols, mixtures of different carboxylic acids as well as mixtures of one or more alcohols and one or more carboxylic acids may be employed in the ring-opening step.

Any of the reaction conditions known in the art to be capable of causing an alcohol and/or carboxylic acid to ring-open an epoxy group may be utilized in this step. For example, the ring-opening may be catalyzed using an acid, including a Lewis acid such as boron trifluoride and/or a protic acid such as acetic acid or sulfuric acid. The mixture of ring-opening reactant (alcohol and/or carboxylic acid) and partially epoxidized unsaturated fatty acid ester(s) may be heated to accelerate the rate of ring-opening and/or to drive the reaction to completion. Purification steps such as washing with water and/or drying may be carried out prior to the acylation step.

Acylation Step

In the acylation step, at least a portion of the hydroxy groups present in the product obtained in the ring-opening step are acylated (i.e., converted to ester groups). The product thereby obtained may be characterized as an acylated fatty acid ester product containing residual unsaturation. In various embodiments of the invention, at least 10%, at least 20%, at least 30%, at least 40%, at least 50%, at least 60%, at least 70%, at least 80%, at least 90% or even 100% of the hydroxy groups are esterified. The acyloxy (ester) groups which are introduced may be of any suitable structure. In one aspect of the invention, the acyloxy groups may comprise branched, linear or cyclic aliphatic (saturated or unsaturated) hydrocarbyl groups, such as C1 to C23 alkyl groups. The hydrocarbyl groups may also be functionalized with heteroatom-containing functional groups. In one embodiment, the acyloxy groups correspond to the structure —O—C(=O)R, wherein R is a linear or branched C1 to C4 alkyl group such as methyl, ethyl, n-propyl, isopropyl, n-butyl, isobutyl, or t-butyl. The acyloxy group may, for example, be an acetoxy group (—O—C(=O)CH$_3$). A given compound or composition in accordance with the present invention may contain more than one type of acyloxy group. The acyloxy group(s) introduced in the acylation step may be the same as or different from the acyloxy group(s) introduced in the ring-opening step, if such ring-opening step has been carried out using one or more carboxylic acids.

The acyloxy groups may be introduced using any of the esterification methods known in the art, such as reaction of the hydroxy groups of the ring-opened intermediate product with a carboxylic acid, a carboxylic acid ester, a carboxylic acid chloride, or a carboxylic acid anhydride. For example, the ring-opened intermediate product may be contacted with acetic anhydride at a temperature and for a time effective for at least a portion of the hydroxy groups to react with the acetic anhydride such that the hydroxy groups are converted to acetoxy groups.

In one embodiment of the invention, the reactant used to convert the hydroxy groups to ester groups is a monocarboxylate reactant, i.e., a compound containing a single functional group capable of reacting with a hydroxy group to form an acyloxy group, such as a monocarboxylic acid, a monocarboxylic acid ester, monocarboxylic acid chloride, or a carboxylic acid mono-anhydride. In another embodiment, however, a polycarboxylate reactant or mixture of polycarboxylate reactants (possibly in combination with one or more mono-carboxylate reactants) is utilized. Such a reactant may be, for example, a polycarboxylic acid, a polycarboxylic acid ester, a polycarboxylic acid chloride, or a carboxylic acid polyanhydride. When such a polycarboxylate reactant is employed, the multiple carboxylate groups are capable of reacting with hydroxy groups on two or more molecules of the ring-opened unsaturated fatty acid ester obtained in the ring-opening step. The polycarboxylate reactant thus may function to link together two or more ring-opened unsaturated fatty acid molecules.

Further Epoxidation Step

A compound or composition useful as a plasticizer is obtained by further epoxidizing the product obtained from the acylation step, wherein at least a portion of the remaining sites of unsaturation are epoxidized to form epoxy groups. In various embodiments of this step, at least 10%, at least 20%, at least 30%, at least 40%, at least 50%, at least 60%, at least 70%, at least 80%, at least 90%, or even 100% of the residual carbon-carbon double bonds are converted to epoxy groups. The conditions and methods used for such conversion may be generally similar to those described previously in connection with the initial epoxidation step.

The product thereby obtained may be generally described as a fatty acid ester which has been functionalized with epoxy, acyloxy and optionally alkoxy groups. The viscosity, oxirane (epoxy) content and other characteristics of the product may be varied and controlled as may be desired by selecting the unsaturated fatty acid ester, alcohol/carboxylic acid and acylation agent starting materials and by varying the reaction conditions used in the aforementioned steps. In one embodiment, the product has an oxirane content of from about 1% to about 10% by weight (inclusive). Oxirane content may be measured by the procedure described in Analytical Chem 36 (1964), pp. 667-668. In another embodiment, the oxirane content of the product is from about 3% to about 5% by weight (inclusive). The viscosity of the product may, in one embodiment of the invention, range from about 10 cps to about 1200 cps (inclusive) at 25° C. Viscosity may be measured by the test method AOCS Jq 1a-64. The Iodine Value (IV) of the product may range from 0 to about 10 (inclusive), in one embodiment of the invention. IV may be measured by the test method AOCS cd 1b-87. In one advantageous embodiment of the invention, the IV of the product is less than 3. The product may, in one embodiment, have an Acid Value (AV) of from 0 to about 10 (inclusive). AV may be measured by test method AV AOCS Te 2a-64. In one advantageous embodiment of the invention, the product has an AV of less than 2.

Uses

The compounds and compositions provided by the present invention may be incorporated in a composition comprising a thermoplastic polymer. Accordingly, in a further aspect the present invention provides a composition comprising a compound or composition as defined above and at least one thermoplastic polymer. The thermoplastic polymer of the compositions of the present invention may be or comprise, for example and without limitation, a vinyl chloride polymer (e.g., PVC) or a vinyl chloride copolymer such as a copolymer selected from the group consisting of vinyl chloride/vinyl acetate copolymers, vinyl chloride/vinylidene chloride copolymers, vinyl chloride/ethylene copolymers and copolymers prepared by grafting vinyl chloride onto ethylene/vinyl acetate copolymer, and mixtures thereof. Other suitable thermoplastic polymers may include, for example, styrenic polymers, poly(meth)acrylates, polyamides, polyolefins and the like. The compounds and compositions of the present invention which are derived from unsaturated fatty acid esters are also useful as components of adhesives, sealants, coatings and the like, generally in combination with one or more thermoplastic polymers.

The thermoplastic polymer-containing compositions of the present invention may be formulated in any manner to provide the required or desired properties. In a particular aspect, a plasticized composition is provided which comprises the compound or composition derived from an unsaturated fatty acid ester and containing epoxy, acyloxy and optionally alkoxy functional groups in an amount of 1 to 100 parts by weight per 100 parts by weight of the thermoplastic polymer. The thermoplastic polymer-containing composition may also contain one or more additional types of additives known in the art, such as, for example, stabilizers, fire retardants, fillers, processing aids, colorants and the like. Any of the conventional compounding methods known in the art of plasticized thermoplastics, such as melt compounding or extruder compounding, may be utilized to prepare the thermoplastic polymer-containing compositions of the present invention. Plastisols may also be prepared using the fatty acid esters functionalized with epoxy, optional alkoxy and acyloxy groups provided by the present invention. The thermoplastic polymer-containing compositions of the present invention may be made into articles and products using a variety of processing methods which include extrusion, injection molding, blow molding, calendering, spreading, coating and the like.

In one embodiment of the invention, a plasticized composition is provided which is comprised of about 40 to about 60 weight % of a polyvinyl chloride (PVC) resin, about 38 to about 58 weight % of fatty acid ester functionalized with epoxy, acyloxy and optionally alkoxy in accordance with the invention, and about 1 to about 2 weight % of metal stabilizer (such as Ca/Zn stearate), the total equaling 100% by weight.

The compounds and compositions in accordance with the present invention which are derived from unsaturated fatty acid esters may be utilized as full or partial replacements for conventional plasticizers, such as phthalate plasticizers, in plasticized thermoplastic formulations. In one embodiment, such plasticized compositions are free of phthalate plasticizer.

EXAMPLES

Example 1

Epoxidized Soybean Oil Containing Methoxy and Acetoxy Groups

A soybean oil functionalized with epoxy, methoxy and acetoxy groups and useful as a plastics additive was prepared in accordance with the following procedure.

1.1 Partial epoxidation of vegetable oil: Placed 300 grams of soybean oil in a one liter three-neck flask and placed the flask in a water bath for heating and cooling purposes. Added 9 grams of formic acid to the oil and heated the mixture to 60° C. and then started adding 64 grams of 35%

$H_2O_2$ over a period of 3 hours. Continued mixing for additional 2 hours or until the iodine value dropped to the 90-100 level (the starting soybean oil had an iodine value of 128-140). After reaching the desired IV, the oil phase was separated, washed once with water and dried under vacuum. This partially epoxidized soy bean oil was used in the next step. The oil obtained had the following analysis:
Oxirane=1.9% Acid Value (AV)=1.6 Iodine Value (IV)=100
1.2 Ring opening step: Oil from step 1.1 was placed in a one liter three neck flask and 0.5 grams of BF) in acetic acid was added and then 150 grams of methanol was flowed to the oil. This mixture was refluxed for 2-3 hrs or until all oxirane had disappeared (as determined by FTIR or AOCS oxirane titration method). Excess methanol was removed under vacuum. This oil, which was used in the next step, had an iodine value of 98-100 and zero oxirane.
Oxirane=0 AV=1.6 IV=97 Hydroxy Number (OH)=81
1.3 Acetylation step: Oil from step 1.2 was placed in a one liter three neck flask and 42 grams of acetic anhydride was added. The mixture was refluxed at 110° C. for 2-4 hours or until FTIR did not show any hydroxy peak. Then this oil was washed twice with water and dried under vacuum. The oil had the following analysis:
IR=No hydroxy peak IV=58
1.4 Final epoxidation step: Oil from step 1.3 was charged to a one liter three neck flask which was placed in a water bath for heating and cooling purposes. Then 150 ml of toluene and 30 grams of formic acid were added. The mixture was heated to 60° C. and then 95 grams of 35% $H_2O_2$ were added continuously to the mixture over 3 hours while it was mixed and kept at about 60° C. Mixing was continued for an additional 2-3 hours or until the iodine value was less than 3. Then the oil/aqueous phase was separated and the aqueous phase was disposed. The oil phase was washed twice with water and then toluene was removed under vacuum and the oil was dried. The final oil had the following analysis:
Oxirane=4.2%
Iodine value=3.6
Acid value=1
Viscosity=750 cps Example 2

Soybean Oil Functionalized with Epoxy, Butyloxy and Acetoxy Groups

This example describes the preparation of a soybean oil that has been reacted to provide epoxy, butyloxy and acetoxy functional groups, the functionalized soybean oil being suitable for use as a plastics additive.
2.1: Partial epoxidation step: This step was conducted in a manner similar to step 1.1 in Example 1.
2.2: Ring opening step: 300 grams of oil from step 2.1 was placed in a one liter three neck flask and 0.5 grams of $BF_3$ in acetic acid was added and 83 grams of butanol was added to the oil. This mixture was refluxed for 3-4 hrs or until no oxirane peak was detected (FTIR or by titration method). Then the excess of butanol was removed under vacuum. This oil had the following analysis:
Oxirane=0 AV=1.06 IV=93 IR=shows hydroxy peak
2.3: Acetylation step: Oil from step 2.2 was placed in a one liter 3 neck flask and 48 grams of acetic anhydride was added and then the mixture was refluxed at 110° C. for 2-4 hours until FTIR did not show any hydroxy peak. Then this oil was washed twice with water and dried under vacuum. This oil had the following analysis:
IR=No hydroxy peak Iodine value=57
2.4: Final epoxidation step: Oil from step 2.3 was charged to a one liter three-neck flask which was placed in a water bath for heating and cooling purposes. Then 150 grams of toluene and 35 grams of formic acid were added. The mixture was heated to 60° C. and then 107 grams of 35% $H_2O_2$ were added continuously to the mixture over 3 hours while it was mixed and kept at about 60° C. Mixing was continued for an additional 2-3 hours or until the iodine value was less than 3. Then the oil/aqueous phase was separated and the aqueous phase was disposed. The oil phase was washed twice with water and then toluene was removed under vacuum. The final oil had the following analysis:
Oxirane=4.35%
Iodine value=1.9
Acid value=2
Viscosity=690 cps Example 3

Soybean Oil Functionalized with Epoxy, Octyloxy and Acetoxy Groups

In this example, soybean oil was reacted to provide epoxy, octyloxy and acetoxy groups.
3.1—Partial epoxidation step: This step was conducted in a manner similar to step 1.1 in Example 1.
3.2—Ring opening step: 300 grams of oil from step 3.1 was placed in a one liter three neck flask and 0.5 grams of $BF_3$ in acetic acid was added and then 150 grams of 2-ethyl hexanol was added to the oil. This mixture was refluxed for 3-4 hrs at 120-130° C. or until no oxirane was detected (FTIR or titration method). Then the excess of 2-ethyl hexanol was removed under vacuum. This oil had the following analysis:
Oxirane=0 AV=1.7 IV=97 IR=shows hydroxy peak
3.3—Acetylation step: Oil from step 3.2 was placed in a one liter 3 neck flask and 43 grams of acetic anhydride was added. The mixture was then refluxed at 110° C. for 2-4 hours or until FTIR did not show any hydroxy peak. Then this oil was washed twice with water and dried under vacuum. The oil thus obtained had the following characteristics:
IR=No hydroxy peak Iodine value=58
3.4 Final epoxidation step: Oil from step 3.3 was charged to a one liter three-neck flask which was placed in a water bath for heating and cooling purposes. Then 150 grams of toluene and 35 grams of formic acid were added. The mixture was heated to 60° C. and then 115 grams of 35% $H_2O_2$ was continuously added to the mixture over 3 hours while it was mixed and kept at about 60° C. Mixing was continued for an additional 2-3 hours or until the iodine value was less than 3. Then the oil/aqueous phase was separated and the aqueous phase was disposed. The oil phase was washed twice with water and then toluene was removed under a vacuum and the oil was dried. The final product had the following analysis:
Oxirane=3.7%
Iodine value=3.8
Acid value=1.9
Viscosity=712 cps Example 4

Soy Fatty Acids Methyl Ester Functionalized with Epoxy, Methoxy and Acetoxy Groups The following steps were used to prepare a soy fatty acids ester that was functionalized with epoxy, methoxy and acetoxy groups.

4.1 Partial epoxidation step: 750 grams of soy fatty acids methyl ester with an iodine value of 130-135 was placed in a 2 liter three-neck flask. The flask was then placed in a water bath for heating and cooling purposes. 18 grams of formic acid and 28 grams of water were added to the oil and the mixture heated to 60° C. The addition of 130 grams of 35% $H_2O_2$ over a period of 3 hours was then started. Mixing was continued for an additional 2 hours or until the iodine value dropped to the 70-80 range. After reaching the desired IV, the oil phase was separated, washed once with water and then dried under a vacuum. This partially epoxidized soy methyl ester was used in the next step. The oil had the following analysis:
Oxirane=2.9% AV=1.6 IV=70

4.2 Ring opening step: 275 grams of methanol was placed in a three neck flask and 0.7 grams of $H_2SO_4$ or $BF_3$ in acetic acid added to it. The oil from step 4.1 was then added to the mixture of methanol and sulfuric acid. This mixture was refluxed for 3-4 hrs at 65-70° C. or until no oxirane peak was detected by FTIR or titration. After completion of the reaction, excess methanol was removed under vacuum. This oil had the following analysis:
Oxirane=0 AV=1.7 IV=70 IR=hydroxy peak 4.3 Acetylation step: Oil from step 4.2 was placed in a two liter three neck flask and then 165 grams of acetic anhydride were added. The mixture was refluxed at 100° C. for 2-4 hours or until the FTIR spectrum did not show any hydroxy peak. Then this oil was washed twice with water and dried under a vacuum. The analysis of the oil found no hydroxy peak and the iodine value was 68.

4.4 Final epoxidation step: Oil from step 4.3 was charged to a two liter three-neck flask which was placed in a water bath for heating and cooling purposes. Then 300 grams of toluene and 60 grams of formic acid was added. The mixture was heated to 60° C. and then 300 grams of 35% $H_2O_2$ was continuously added to the mixture over 3 hours while it was mixed and kept at about 60° C. Mixing was continued for an additional 2-3 hours or until the iodine value was less than 5. Then the oil/aqueous phase was separated and the aqueous phase was disposed. The oil phase was washed twice with water and then the toluene was removed under a vacuum and the oil was dried. The final oil had the following analysis:
Oxirane=4%
Iodine value=3
Acid value=2.7
Viscosity=28 cps Example 5

Soy Fatty Acids Methyl Ester Functionalized with Epoxy, Butyloxy and Acetoxy Groups The same procedure as in Example 4 was used to prepare this product, but butyl alcohol was used in place of methanol. The final product obtained in this example had the following analysis:
Oxirane=4%
Iodine value=3
Acid value=3.2
Viscosity=28 cps Example 6

Soy Fatty Acids Methyl Ester Functionalized with Epoxy, Octyloxy and Acetoxy Groups This product was prepared in accordance with the procedures of Example 5, except that 2-ethyl hexyl alcohol was used in place of methanol.

The product obtained from this example had the following analysis:
Oxirane=4.1%
Iodine value=2.8
Acid value=3.8
Viscosity=29 cps Example 7

Ring Opening with Acetic Acid

This example demonstrates the preparation of a soybean oil functionalized with epoxy and acetoxy groups, wherein the ring-opening was carried out using a carboxylic acid (acetic acid).

7.1. Partial epoxidation step: This step was conducted in a manner similar to step 1.1 in Example 1.

7.2. Ring opening step: Oil from step 7.1 was placed in a one liter three neck flask and 0.5 grams of $BF_3$ in acetic acid added and then 120 grams of acetic acid was flowed to the oil. This mixture was refluxed for 2-3 hrs or until all oxirane disappeared (as determined by FTIR or AOCS oxirane titration method). Excess acetic acid was removed under vacuum. This oil, which was used in the next step, had an iodine value of 98-100 and zero oxirane; IR analysis indicated the formation of OH groups.

7.3 Acetylation step: Oil from step 7.2 was placed in a one liter three neck flask and 50 grams of acetic anhydride was added. The mixture was refluxed at 110° C. for 2-4 hours or until FTIR did not show any hydroxy peak. Then excess acetic acid was removed under vacuum. The oil obtained had the following analysis:
IR=No hydroxy peak IV=86

7.4 Final epoxidation step: Oil from step 7.3 which contained fatty acid ester moieties containing two adjacent acetoxy groups was charged to a one liter three neck flask which was placed in a water bath for heating and cooling purposes. Then 150 ml of toluene and 30 grams of formic acid were added. The mixture was heated to 60° C. and then 150 grams of 35% $H_2O_2$ were added continuously to the mixture over 3 hours while it was mixed and kept at about 60° C. Mixing was continued for an additional 2-3 hours or until the iodine value was less than 3. Then the oil/aqueous phases were separated and the aqueous phase was disposed. The oil phase was washed twice with water and then toluene was removed under vacuum and the oil was dried. The final oil had the following analysis:
Oxirane=4.66% Iodine value=2 Acid Value=1 Viscosity=1542 cps Example 8

Ring-Opening using Neooctanoic Acid 8.1: Partial epoxidation step: This step was conducted in a manner similar to Step 1.1 in Example 1.

8.2: Ring opening step: 300 grams of oil from step 8.1 was placed in a one liter three neck flask and 0.5 grams of $BF_3$ in acetic acid and 100 grams of neooctanoic acid were added to the oil. This mixture was refluxed for 3-4 hrs or until no oxirane peak could be detected (by FTIR or by titration method). Then the excess of neooctanoic acid was removed under vacuum. This oil had the following analysis:
Oxirane=0 AV=1.06 IV=93 IR=hydroxy peak present 8.3: Acetylation step: Oil from step 8.2 was placed in a one liter 3 neck flask and 48 grams of acetic anhydride was added. The mixture was then refluxed at 110° C. for 2-4 hours until FTIR did not show any hydroxy peak. This oil was then washed twice with water and dried under vacuum. The oil thus obtained had the following analysis:
IR=No hydroxy peak present Iodine value=83
8.4: Final epoxidation step: Oil from step 8.3 was charged to a one liter three-neck flask which was placed in a water bath for heating and cooling purposes. Then 150 grams of toluene and 35 grams of formic acid were added. The mixture was heated to 60° C. and then 110 grams of 35% $H_2O_2$ were added continuously to the mixture over 3 hours while it was mixed and kept at about 60° C. Mixing was continued for an additional 2-3 hours or until the iodine value was less than 3. Then the oil/aqueous phases were separated and the aqueous phase was disposed. The oil phase was washed twice with water and then toluene was removed under vacuum. The final oil had the following analysis:
Oxirane=4.2% Iodine value=2.6 Acid value=2 Viscosity=1184 cps Example 9

Soy Fatty Acids Methyl Ester Functionalized with Epoxy, Octylacyl and Acetoxy Groups This example was performed in a manner similar to Example 8 but soy fatty acid methyl ester was used in place of soybean oil. The product obtained from this reaction had the following analysis:
Oxirane=4.25% Iodine value=2 Acid value=2.8 Viscosity=60 cps

What is claimed is:

1. A composition comprising a fatty acid ester moiety, wherein the fatty acid ester moiety comprises at least one epoxy group and wherein the fatty acid ester moiety is substituted at least with a first substituent which is a first acyloxy group and with a second substituent which is a second acyloxy group, which may be the same as or different from the first acyloxy group, or an alkoxy group, wherein the first substituent and the second substituent are substituted on adjacent carbon atoms in the fatty acid ester moiety.

2. The composition of claim 1, wherein the fatty acid ester moiety is selected from the group consisting of fatty acid monoesters, monoglycerides, diglycerides, triglycerides, and fatty acid esters of polyols other than glycerin.

3. The composition of claim 1, wherein the first acyloxy group is a C2-C24 aliphatic acyloxy group.

4. The composition of claim 1, wherein the first acyloxy group has a structure R—C(=O)—O—, wherein R is a straight chain, branched or alicyclic, saturated or unsaturated hydrocarbyl group containing one to 23 carbon atoms.

5. The composition of claim 1, wherein the first acyloxy group is an acetoxy group.

6. The composition of claim 1, wherein the second substituent is a C2-C24 aliphatic acyloxy group.

7. The composition of claim 1, wherein the second substituent has a structure R—C(=O)—O—, wherein R is a straight chain, branched or alicyclic, saturated or unsaturated hydrocarbyl group containing one to 23 carbon atoms.

8. The composition of claim 1, wherein the second substituent is a C1-C24 alkoxy group.

9. The composition of claim 1, wherein the second substituent has a structure R1-O—, wherein R1 is a straight chain, branched or alicyclic, saturated or unsaturated hydrocarbyl group containing one to 23 carbon atoms.

10. The composition of claim 9, wherein R1 is a straight or branched chain saturated hydrocarbyl group containing one to ten carbon atoms.

11. The composition of claim 1, comprising a first fatty acid ester moiety and second fatty acid ester moiety which are linked together through a polyfunctional alkoxy group, a polyfunctional acyloxy group, or a polyfunctional alkoxy/acyloxy group.

* * * * *